United States Patent [19]
Wolf et al.

[11] Patent Number: 5,357,955
[45] Date of Patent: Oct. 25, 1994

[54] REINFORCED CATHETER PROBE

[75] Inventors: Erich H. Wolf, Vista; Christopher L. Davis; David P. Skarshaug, both of San Diego; Charles S. Bankert, Oceanside; Richard Hannah, Vista; Samuel D. Riccitelli, Carlsbad, all of Calif.

[73] Assignee: Puritan-Bennett Corporation, Carlsbad, Calif.

[21] Appl. No.: 185,777

[22] Filed: Jan. 24, 1994

Related U.S. Application Data

[63] Continuation of Ser. No. 888,545, May 22, 1992, abandoned.

[51] Int. Cl.$^5$ ............................................. A61B 5/00
[52] U.S. Cl. ................................. 128/634; 604/282
[58] Field of Search ......................... 128/633–634, 128/632, 664–667, 636; 604/264, 280, 282, 164–165, 167–169, 273

[56] References Cited

U.S. PATENT DOCUMENTS

| | | | |
|---|---|---|---|
| 4,626,067 | 12/1986 | Watson | 385/86 |
| 4,706,677 | 11/1987 | Goorsky et al. | |
| 4,727,730 | 3/1988 | Boiarski et al. | |
| 4,730,622 | 3/1988 | Cohen | 128/667 |
| 4,800,886 | 1/1989 | Nestor | |
| 4,830,013 | 5/1989 | Maxwell | |
| 4,854,321 | 8/1989 | Boiarski | |
| 4,861,727 | 8/1989 | Hauenstein et al. | |
| 4,889,407 | 12/1989 | Markle et al. | |
| 4,900,381 | 2/1990 | Guenther et al. | |
| 4,919,891 | 4/1990 | Yafuso et al. | |
| 4,925,268 | 5/1990 | Iyer et al. | |
| 4,960,412 | 10/1990 | Fink | 604/167 |
| 5,005,576 | 4/1991 | Günther | 128/634 |
| 5,020,537 | 6/1991 | Günther | 128/634 |

FOREIGN PATENT DOCUMENTS

0336984A1 10/1989 European Pat. Off. .
0336985A1 10/1989 European Pat. Off. .

*Primary Examiner*—Angela D. Sykes
*Attorney, Agent, or Firm*—Fulwider Patton Lee & Utecht

[57] ABSTRACT

The reinforced catheter sensor probe for intravascular use includes an aramid strand that extends along the length of the electromagnetic conduits and is bonded thereto. A greater than ten fold increase in tensile strength is thereby achieved. Additionally, the inherent strength of flexibility of the reinforcing strand ensures that a positive interconnection with the distal end of the sensor probe is maintained in the event the sensor probe is subjected to loads that cause its relatively more fragile components to sever. A protective, strain relieving introducer catheter is also provided to substantially prevent kinking and breakage of the sensor probe where the introducer catheter bends.

21 Claims, 1 Drawing Sheet

REINFORCED CATHETER PROBE

This application is a continuation of application Ser. No. 07/888,545, filed May 22, 1992, now abandoned.

BACKGROUND OF THE INVENTION

1. Field of the Invention

The present invention relates generally to reinforced catheter probe structures and more particularly pertains to the enhancement of the tensile strength of optical fiber containing sensor devices that are intended for intravascular introduction so as to effectively minimize or preclude the risk of detachment of a distal portion thereof.

2. Description of the Prior Art

A variety of sensor systems have been developed that require the introduction of an optical fiber or optical fiber bundle into a patient's vasculature in order to obtain real time measurement of certain physiological parameters. In order to expand the capabilities of such systems, sensor probes are being called upon to accommodate an increasing number of components therein while maintaining a very small outside diameter. These requirements constrain the individual components to be of reduced size and consequently, optical fibers of very small cross-section are used. Such optical fibers are relatively delicate and have little individual strength. Furthermore, when the optical fibers are displaced about the central axis of the sensor probe, they are subjected to increased stress in bending and are thus more susceptible to fracture. Invasive optical blood gas analyzers have been proposed that employ a sensor probe incorporating a plurality of optical fibers for sensing a number of parameters, including the partial pressure of oxygen, the partial pressure of carbon dioxide, pH and blood temperature. Such sensors are particularly susceptible to fracture of the fibers due to bending or rough use.

Mechanical failure of such a sensor probe while it is inserted within a patient's vasculature could result in a portion of the sensor probe being carried into the blood stream with the resultant undesirable consequences, especially if the severed section of the sensor probe were carried to a critical area within the vasculature. It is therefore desirable to provide sensor probes with an internal member having sufficient tensile strength to avoid the likelihood of severance of a portion of the sensor probe tip if the fibers in the sensor probe are broken.

An additional important consideration in the design of such sensor probes is cost. Such sensor probes are intended for a one-time use only and risks of infection and the degradation of the sensors performance upon resterilization preclude the re-use of such devices. The sensor probes, including any provisions for enhancing tensile strength, must therefore be manufacturable as inexpensively as possible in order to render their disposability economically feasible.

The mechanical strength and more particularly, the tensile strength of some prior art optical fiber-containing sensor probe systems has been increased by the incorporation of a stainless steel wire disposed within the sensor probe and parallel to the optical fibers. The distal end of the wire is welded to a stainless steel spherical anchor element, the outer diameter of which conforms to or slightly exceeds the outer diameter of a sheath that envelops the optical fiber bundle. A portion of the sheath may similarly be constructed of stainless steel and welded to the anchor element. While such a configuration presumably imparts substantial tensile strength to the sensor probe system and prevents detachment of the tip if the optical fibers are broken, this configuration is incompatible with systems that require the distal end of the sensor probe to be fully exposed to blood flow. Further, the stainless steel components and the rather labor-intensive effort required for its assembly add substantial cost to the sensor probe.

It has also been found that optical fiber based sensor probes have a tendency to break where the strain of bending is imposed on the sensor probe. Such sensor probes are typically disposed within a conventional introducer catheter having a relatively inflexible hub or funnel portion and a relatively flexible elongated tubular portion. Breakage of the sensor typically occurs at the junction of the hub and flexible tubular portion within the introducer catheter due to the force of bending which can be imposed on the optical fiber portion of the sensor probe there.

It would be highly advantageous if a low cost means were available which substantially enhanced the tensile strength of an optical fiber sensor probe system, particularly if one or more optical fibers is fractured, allowed free access of an analyte to the distal end of the sensor probe and which protected and did not impair the flexibility of the sensor probe. The present invention provides such a capability.

SUMMARY OF THE INVENTION

The present invention provides an optical fiber bundle containing sensor probe structure of enhanced tensile strength and resistance to separation. The structure employs low cost components, is quickly and easily assembled, does not impair access of the analyte to the distal end of the sensor probe and does not materially reduce the flexibility of the sensor probe.

The sensor probe of the present invention incorporates at least one electromagnetic conduit such as optical fibers utilized to sense the presence of gaseous oxygen and carbon dioxide or blood pH. A thin, highly flexible reinforcing strand is disposed parallel to the fibers and is attached thereto. In a presently preferred embodiment, the strand is attached by thermoplastic shrink tubing that attaches the strand to the conduit bundle near the proximal and distal ends of the strand. The entire assembly is encased in heat shrink tubing. Heat used to shrink the tubing melts the thermoplastic shrink tube to firmly adhere the strand to the sensor bundle. The tensile strength of a sensor probe is thereby greatly increased, generally by greater than one order of magnitude, and in the other event the relatively fragile components of the sensor probe such as the optical fibers fail structurally, the reinforcing strand direct interconnection with the sensor probe distal end ensures that all components of the sensor probe are retrieved upon retraction. This desirable result is achieved with the use of very inexpensive materials and a minimal amount of labor. In other preferred embodiments, adhesive means may be used to attach the strand to the fibers.

In another aspect of the invention, the reinforced sensor probe structure preferably includes an introducer catheter having a generally smooth inner lumen in which at least a portion of the sensor probe is disposed, in order to protect the sensor probe from breaking. The introducer catheter includes a relatively inflexible, rigid proximal introducer hub and a distal relatively flexible, elongate hollow tubular member connected to the introducer hub, and a strain relief member disposed over the junction between the introducer hub and the elongate hollow tubular member. The strain relief member thus allows the optical fibers and the reinforcing strand to bend to a limited degree to protect and substantially prevent kinking and breakage of said optical fiber at said junction between said introducer hub and said elongate hollow tubular member. The combination of the reinforced probe sensor and the protective introducer catheter provide for a reinforced catheter probe structure which is highly resistive to breakage of the sensor probe system.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENT

The present invention is embodied in a reinforced catheter sensor probe structure of the type used to measure blood chemistry by means of optical fiber sensors embedded in a polymer structure. In one aspect of the invention the reinforced catheter sensor probe structure includes a flexible, high tensile strength reinforcing strand disposed parallel with optical fibers in the sensor probe and attached thereto to prevent separation of the tip of the sensor probe in the event of fracture of one or more of the optical fibers. In another aspect of the invention, the reinforced catheter sensor probe structure includes a protective, strain relieving introducer catheter in which the sensor probe is disposed. The sensor probe is introduced into a patient's vasculature whereby an analytical instrument interconnected thereto is then able to provide a real time measurement of the oxygen and carbon dioxide content and pH of the blood.

Figure 1:
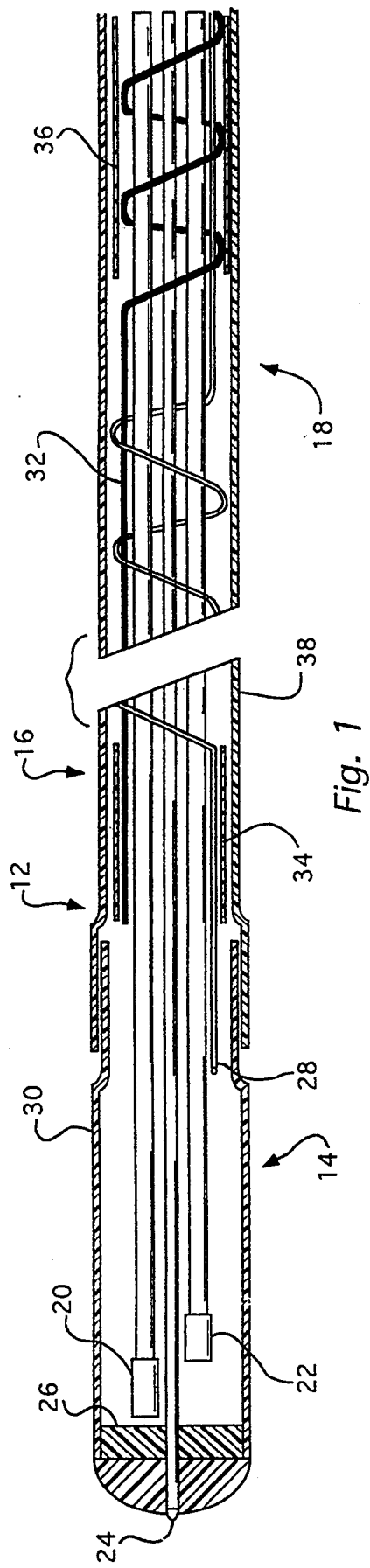
FIG. 1 is an enlarged cross-sectional view of a preferred embodiment of a sensor probe incorporating the reinforced structure of the present invention.
Figure 2:
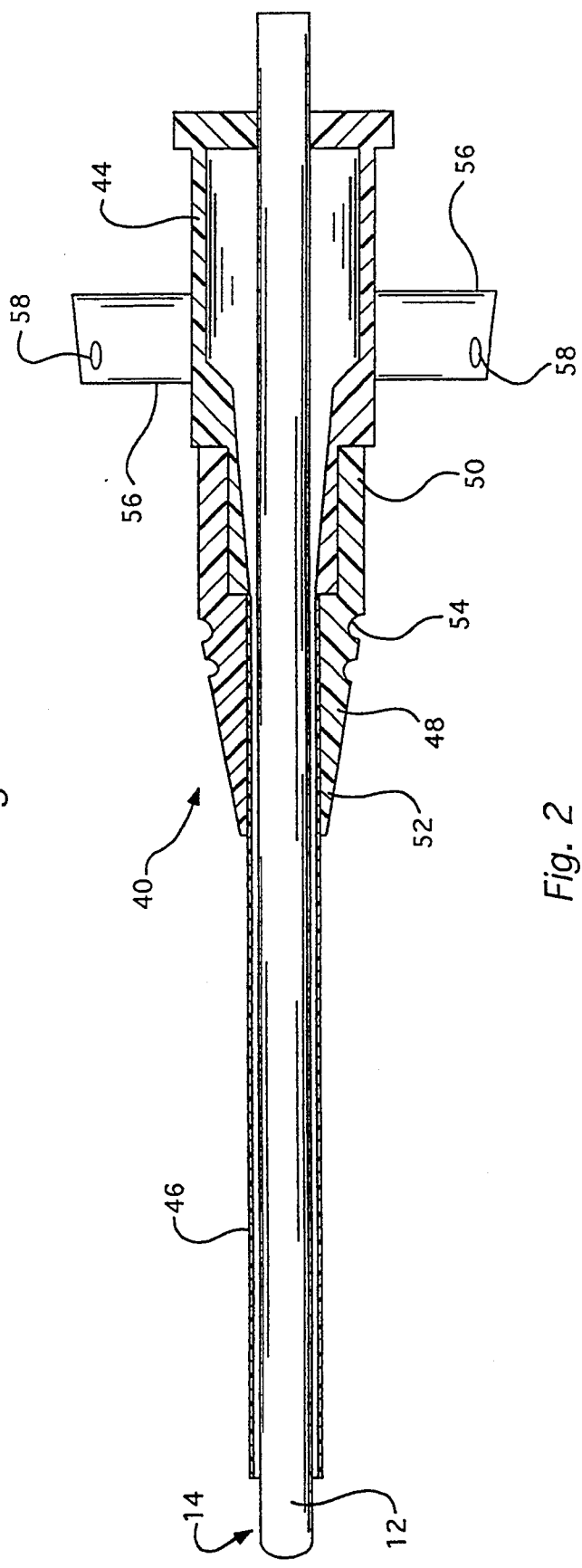
FIG. 2 is an enlarged cross-sectional view of the reinforced sensor probe of the invention disposed within a strain relieving introducer catheter.

With reference to FIG. 1, the sensor probe 12 consists of a distal probe sensor section 14, an intermediate tubular section 16 and a proximal portion 18 of the intermediate tubular section which terminates in a coupling (not shown) for interconnection to an analytical instrument (not shown). The sensor probe accommodates a plurality of individual sensors that are disposed within and extend through the intermediate tubular section to terminate in the distal probe sensor section. An oxygen sensor 20 and a carbon dioxide sensor 22 are preferably provided in the sensor probe, each consisting of an electromagnetic conduit portion that preferably comprises an optical fiber, having a sensing element containing specially selected oxygen and carbon dioxide sensitive compounds deposited thereon near the distal ends of the sensors, respectively.

A pH sensor 24 also preferably is disposed within and extends into the distal end of the probe sensor section 14, and is centered within the distal probe sensor section by a silicone spacer 26. Thermocouple 28 may additionally be accommodated in the probe sensor section. The probe sensor section 14 is encased in an analyte permeable sleeve 30 that is preferably formed of silicone. The sensors 20, 22, and 24 are typically provided with means of communication with the analytical instrument via an electro-optical coupler disposed at their proximal ends.

The intermediate tubular section 16 incorporates the reinforced structure of the sensor probe of the present invention. A reinforcing strand 32 is included in the conduit bundle and extends from near the terminus of the probe section's silicone sleeve 30 to a position along the sensor probe that remains outside of the patient at all times. While a variety of reinforcing materials could be used, provided that they displayed the requisite tensile strength, flexibility, resistance to fatigue and bondability to the optical fiber structure, the reinforcing strand of a presently preferred embodiment consists of one or more aramid fibers such as are available under the trade mark Kevlar ®.

In constructing the catheter, thermoplastic shrink tubing members 34, 36 (preferably comprising nylon) are attached around the entire sensor bundle near the proximal end and the distal end of the reinforcing strand. A section of heat shrink tubing 38, preferably formed of tetrafluoroethylene (TFE) is positioned along the sensor probe's entire length up to the silicone sleeve 30. Upon exposure to sufficient heat to shrink the heat shrink tubing 38, the thermoplastic members 34, 36 melt to positively affix the ends of the reinforcing strand to the optical fiber bundle.

In another preferred embodiment, the strand 32 is adhesively bonded to one or more optical fibers within the catheter. One benefit to such a construction is that the strength of the strand contributes directly to the reinforcement of the optical fibers to which the strand is bonded, thereby preventing the progressive rupture of fibers and potential dislodging of the tip prior to the strength of the fiber coming into play.

Tests have shown that a sensor probe constructed as described above, when broken, is capable of withstanding a tensile force of 8.74 lbs. while a similar construction sans reinforcing fiber 32, when broken, is capable of withstanding a tensile force of only 0.49 lbs. The extremely flexible nature of the reinforcing fibers does not impair the sensor probe's flexibility, while its attachment directly to the sensor bundle obviates the need to utilize any special anchoring fittings that could increase costs and impair the performance of the probe. Additionally, due to the inherent flexibility and strength of the reinforcing strand, it is capable of withstanding loads that would cause the more fragile components of the sensor probe to detach and is thereby able to continue to provide a positive interconnection with the sensor probe's distal end in order to facilitate complete retrieval of all portions of the sensor probe from within the body.

The reinforced catheter sensor probe structure preferably also includes an introducer catheter 40 having a generally smooth inner lumen 42 in which at least a portion of the optical fiber and said reinforcing strand of the sensor probe are disposed. The introducer catheter comprises a relatively inflexible, rigid proximal introducer hub or funnel portion 44, and a distal relatively flexible, elongate hollow tubular member 46 connected to the introducer hub. The hub or funnel portion is typically formed of relatively rigid, inflexible material, such as polypropylene, ABS plastic, or nylon, while the elongate tubular portion is typically formed of a relatively flexible, elastomeric material such as polyurethane or TFE. The junction of the distal tubular member to the introducer hub is preferably disposed within a strain relief member 48 which snugly fits over the introducer hub and the elongate hollow tubular member allowing limited bending of the hollow tubular portion of the introducer catheter, and thus allowing the optical fiber and the reinforcing strand to bend to a limited degree within the introducer catheter.

The strain relief member is preferably tapered from a relatively wider proximal section 50 connected to said introducer hub, to a relatively narrow distal section 52 connected to said elongate hollow tubular member. The strain relief member also preferably includes at least one constriction 54 of reduced cross-sectional thickness, and most preferably two such constrictions, allowing the strain relief member to bend. The strain relief member of the introducer catheter can thereby substantially prevent kinking and breakage of the optical fiber at the junction between the introducer hub and the elongate hollow tubular member. Extensions 56 may also be provided on the introducer catheter that include suture holes 58, for secure placement of the combination of the strain relieving introducer catheter and the reinforced sensor probe.

While a particular form of the invention has been illustrated and described, it will also be apparent to those skilled in the art that various modifications can be made without departing from the spirit and scope of the invention. For example, those skilled in the art will also recognize that a variety of other sensor probes for medical use, such as imaging probes, may also enjoy benefits from the use of the invention, particularly if the sensor probe has delicate portions which are capable of being dislodged if the optical fiber or other structure is severed or ruptured. Accordingly, it is not intended that the invention be limited except as by the appended claims.

What is claimed is:

1. A reinforced sensor probe structure comprising:
   at least one optical fiber having a distal end, an intermediate portion and a proximal portion;
   an analyte sensor disposed on said distal end of said optical fiber;
   an analyte permeable sleeve disposed over said distal end of said optical fiber, said analyte permeable sleeve having a proximal end and a distal end;
   a reinforcing strand attached to said optical fiber proximal portion and also attached to said optical fiber near said distal end of said optical fiber proximal to said analyte permeable sleeve, to maintain a positive linkage of said proximal end of said optical fiber with said distal end of said optical fiber in the event the optical fiber ruptures; and
   a heat shrink tubing member extending over at least the proximal end of said analyte permeable sleeve, and a portion of said reinforcing strand, to maintain a positive linkage of said analyte permeable sleeve with said optical fiber in the event the optical fiber ruptures.

2. The sensor probe structure of claim 1 wherein said reinforcing strand is attached to said optical fiber by a melted thermoplastic material.

3. The sensor probe structure of claim 1 wherein said reinforcing strand is attached to said optical fiber by a melted nylon shrink tube.

4. The sensor probe structure of claim 1 wherein said reinforcing strand is attached to said optical fiber by an adhesive.

5. The sensor probe structure of claim 1 wherein said reinforcing strand comprises at least one aramid fiber.

6. The sensor probe structure of claim 1, further including an introducer catheter having a smooth inner lumen in which at least a portion of said optical fiber and said reinforcing strand are disposed, said introducer catheter comprising a relatively inflexible, rigid proximal introducer hub, a distal relatively flexible, elongate hollow tubular member connected to said introducer hub at a junction therebetween, and a strain relief member disposed over said junction between said introducer hub and said elongate hollow tubular member allowing said optical fiber and said reinforcing strand to bend to a limited degree therein to thereby substantially prevent kinking and breakage of said optical fiber at said junction between said introducer hub and said elongate hollow tubular member.

7. The sensor probe structure of claim 6, wherein said strain relief member is tapered from a relatively wider proximal section connected to said introducer hub, to a relatively narrow distal section connected to said elongate hollow tubular member.

8. The sensor probe structure of claim 7, wherein said strain relief member includes at least one constriction of reduced cross-sectional thickness allowing said strain relief member to bend.

9. A reinforced sensor probe structure comprising:
   an analyte permeable sleeve having a proximal end and a distal end;
   a bundle of electromagnetic conduits disposed within and extending through said analyte permeable sleeve, said bundle of electromagnetic conduits being secured to one another and having a proximal end, an intermediate portion and a distal end;
   a highly flexible reinforcing strand secured to said proximal end and said distal end of said conduit bundle, said reinforcing strand having a proximal end and a distal end; and
   means for positively securing said conduits to said analyte permeable sleeve.

10. The sensor probe of claim 9 wherein said reinforcing strand comprises at least one aramid fiber.

11. The sensor probe of claim 9, wherein said means for securing said conduits to said analyte permeable tubular sleeve comprises an enveloping sheath of heat shrink tubing extending over said proximal end of said analyte permeable tubular sleeve, said distal end of said reinforcing strand, and said intermediate portion of said conduit bundle.

12. The sensor probe structure of claim 9, wherein said bundle of electromagnetic conduits includes at least one optical fiber, and further including an introducer catheter having a smooth inner lumen in which at least a portion of said optical fiber and said reinforcing strand are disposed, said introducer catheter comprising a relatively inflexible, rigid proximal introducer hub, a distal relatively flexible, elongate hollow tubular member connected to said introducer hub at a junction therebetween, and a strain relief member disposed about junction between said introducer hub and said elongate hollow tubular member allowing said optical fiber and said reinforcing strand to bend to a limited degree therein to thereby substantially prevent kinking and breakage of said optical fiber at said junction between said introducer hub and said elongate hollow tubular member.

13. The sensor probe structure of claim 12, wherein said strain relief member is tapered from a relatively wider proximal section connected to said introducer hub, to a relatively narrow distal section connected to said elongate hollow tubular member.

14. The sensor probe structure of claim 13, wherein said strain relief member includes a plurality of constrictions of reduced cross-sectional thickness allowing said strain relief member to bend.

15. An intravascular sensor probe for the sensing of a plurality of analytes, comprising:
- a plurality of electromagnetic conduits each having a proximal end, an intermediate portion, and a distal end.
- an analyte permeable tubular member disposed over said distal ends of said plurality of electromagnetic conduits, said analyte permeable tubular member having a proximal end and a distal end;
- an aramid strand disposed in parallel with said conduits;
- means for positively joining said conduits and strand to one another near said proximal and distal ends of said electromagnetic conduits; and
- an external sheath disposed tightly over and securing said proximal end of said analyte permeable tubular member to said aramid strand and said intermediate portion of said electromagnetic conduits.

16. The sensor probe of claim 15 wherein said means for positively joining comprises a melted thermoplastic material.

17. The sensor probe of claim 16 wherein said joining means comprises a thermoplastic tube melted about said conduits and said aramid strand.

18. The sensor probe of claim 17 wherein said thermoplastic material comprises nylon.

19. The sensor probe structure of claim 15, wherein said electromagnetic conduits includes at least one optical fiber, further including an introducer catheter having a smooth inner lumen in which at least a portion of said optical fiber and said reinforcing strand are disposed, said introducer catheter comprising a relatively inflexible, rigid proximal introducer hub, a distal relatively flexible, elongate hollow tubular member connected to said introducer hub at a junction therebetween, and a strain relief member disposed about said junction between said introducer hub and said elongate hollow tubular member allowing said optical fiber and said reinforcing strand to bend to a limited degree therein to thereby substantially prevent kinking and breakage of said optical fiber at said junction between said introducer hub and said elongate hollow tubular member.

20. The sensor probe structure of claim 19, wherein said strain relief member is tapered from a relatively wider proximal section connected to said introducer hub, to a relatively narrow distal section connected to said elongate hollow tubular member.

21. The sensor probe structure of claim 20, wherein said strain relief member includes at least one constriction of reduced cross-sectional thickness allowing said strain relief member to bend.

* * * * *